(12) United States Patent
Shin et al.

(10) Patent No.: US 7,750,176 B2
(45) Date of Patent: Jul. 6, 2010

(54) MULTI-FUNCTIONAL CYCLIC SILOXANE COMPOUND AND PROCESS FOR PREPARING DIELECTRIC FILM BY USING SILOXANE-BASED POLYMER PREPARED FROM THE COMPOUND

(75) Inventors: Hyeon Jin Shin, Gyeonggi-Do (KR); Hyun Dam Jeong, Gyeonggi-Do (KR); Jong Baek Seon, Gyeonggi-Do (KR); Sang Kook Mah, Seoul (KR); Jin Heong Yim, Gyeonggi-Do (KR); Jae Jun Lee, Gyeonggi-Do (KR); Kwang Hee Lee, Gyeonggi-Do (KR); Jung Bae Kim, Gyeonggi-Do (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 12/458,009

(22) Filed: Jun. 29, 2009

(65) Prior Publication Data
US 2009/0269942 A1  Oct. 29, 2009

Related U.S. Application Data

(62) Division of application No. 10/878,119, filed on Jun. 29, 2004, now Pat. No. 7,576,230.

(30) Foreign Application Priority Data

| Jun. 30, 2003 | (KR) | ............................... 2003-43558 |
| Nov. 5, 2003 | (KR) | ............................... 2003-78009 |
| Jun. 10, 2004 | (KR) | ............................... 2004-42522 |

(51) Int. Cl.
*C07F 7/08* (2006.01)
*C08G 77/04* (2006.01)
*B32B 9/04* (2006.01)

(52) U.S. Cl. ........................... 556/460; 528/33; 528/37; 428/447

(58) Field of Classification Search ................... 528/33, 528/37; 556/460
See application file for complete search history.

(56) References Cited

U.S. PATENT DOCUMENTS

| 3,528,941 | A | 9/1970 | Murphy |
| 3,615,272 | A | 10/1971 | Collins et al. |
| 4,399,266 | A | 8/1983 | Matsumura et al. |
| 4,756,977 | A | 7/1988 | Haluska et al. |
| 4,999,397 | A | 3/1991 | Weiss et al. |
| 5,010,159 | A | 4/1991 | Bank et al. |
| 5,378,790 | A | 1/1995 | Michalczyk et al. |
| 5,698,654 | A | 12/1997 | Nye et al. |
| 5,853,808 | A | 12/1998 | Arkles et al. |
| 6,000,339 | A | 12/1999 | Matsuzawa |
| 6,232,424 | B1 | 5/2001 | Zhong et al. |
| 6,410,150 | B1 | 6/2002 | Kurosawa et al. |
| 6,660,822 | B2 | 12/2003 | Lyu et al. |
| 6,740,602 | B1 | 5/2004 | Hendriks et al. |
| 6,841,197 | B2 | 1/2005 | Standke et al. |

FOREIGN PATENT DOCUMENTS

| EP | 0997497 | 7/1998 |
| EP | 1205481 | 5/2002 |
| JP | 2000-309753 A | 11/2000 |
| JP | 2002-231715 A | 8/2002 |
| JP | 2005-523377 A | 8/2005 |
| WO | WO 99/03926 A1 | 1/1999 |

OTHER PUBLICATIONS

Cai et al., *Macromolecules*, vol. 33, No. 17, p. 6310-6314 (2000).
Shchegolikhina et al., *Inorganic Chemistry*, vol. 41, No. 25, p. 6892-6904 (2002).
Okawara et al., *Bulletin of the Chemical Society of Japan*, vol. 31, No. 1, p. 22-25 (1958).
Lee et al., *Polymer Journal*, vol. 30, No. 9, p. 730-735 (1998).
Japanese Office Action dated Sep. 29, 2009 in corresponding Japanese Application No. 2004-188031.

*Primary Examiner*—Randy Gulakowski
*Assistant Examiner*—Robert Loewe
(74) *Attorney, Agent, or Firm*—Harness, Dickey & Pierce, P.L.C.

(57) ABSTRACT

A multi-functional cyclic siloxane compound (A), a siloxane-based (co)polymer prepared from the compound (A), or compound (A) and at least one of a Si monomer having organic bridges (B), an acyclic alkoxy silane monomer (C), and a linear siloxane monomer (D); and a process for preparing a dielectric film using the polymer. The siloxane compound of the present invention is highly reactive, so the polymer prepared from the compound is excellent in mechanical properties, thermal stability and crack resistance, and has a low dielectric constant resulting from compatibility with conventional pore-generating materials. Furthermore, a low content of carbon and high content of $SiO_2$ enhance its applicability to the process of producing a semiconductor, wherein it finds great use as a dielectric film.

8 Claims, No Drawings

MULTI-FUNCTIONAL CYCLIC SILOXANE COMPOUND AND PROCESS FOR PREPARING DIELECTRIC FILM BY USING SILOXANE-BASED POLYMER PREPARED FROM THE COMPOUND

PRIORITY STATEMENT

This non-provisional application is a divisional application of U.S. Ser. No. 10/878,119, filed Jun. 29, 2004 now U.S. Pat. No. 7,576,230, the entire contents of which are incorporated herein by reference, which claims priority under 35 U.S.C. 119(a) on Korean Patent Application Nos. 2003-43558 filed on Jun. 30, 2003; 2003-78009 filed on Nov. 5, 2003; and 2004-42522 filed on Jun. 10, 2004, the entire contents of each of which are incorporated herein by reference.

BACKGROUND OF THE INVENTION

1. Field of the Invention

The present invention relates to a multi-functional cyclic siloxane compound, a siloxane-based polymer prepared from the compound and a process for preparing a dielectric film using the polymer. More specifically, the present invention relates to a multi-functional cyclic siloxane compound (A); a siloxane-based (co)polymer prepared from the compound (A), or the compound (A) and at least one of Si monomer (B) having organic bridges, acyclic alkoxy silane monomer (C), and linear siloxane monomer (D) and a process for preparing a dielectric film using the polymer.

2. Description of the Related Art

As the degree of integration in semiconductor devices increases, R (resistance)×C (capacitance) delay also increases, resulting in serious problems such as a signaling transfer delay. So, how to reduce the capacitance of an interlayer dielectric film has been a matter of the greatest concerns in the field of semiconductor production technology, and various attempts have been made to develop low dielectric materials for use in the production of enhanced dielectric films.

For example, U.S. Pat. Nos. 3,615,272; 4,399,266; 4,756,977; and 4,999,397 disclose dielectric films produced by spin on deposition (SOD) using polysilsesquioxanes (dielectric constant: about 2.5-3.1) instead of $SiO_2$ (dielectric constant: 4.0) that should be deposited by chemical vapor deposition (CVD). Also, hydrogensilsesquioxanes as well as methods for their preparation are well known in the art. For example, U.S. Pat. No. 3,615,272 discloses a method of preparing a completely condensed, soluble hydrogensilsesquioxane, which comprises the steps of condensing trichloro-, trimethoxy- and triacetoxy-silanes in a sulfuric acid medium and then washing the resulting resin with water or aqueous sulfuric acid. U.S. Pat. No. 5,010,159 also discloses a method of synthesizing a condensed hydrogensilsesquioxane resin, which comprises the steps of hydrolyzing hydrosilanes in an arylsulfuric acid hydrate-containing hydrolysis medium and then contacting the resulting resin with a neutralizing agent. U.S. Pat. No. 6,232,424 describes a highly soluble silicone resin composition very stable in solution, which is prepared by hydrolyzing and polycondensing tetraalkoxysilane, organosilane and organotrialkoxysilane monomers in the presence of water and an appropriate catalyst. U.S. Pat. No. 6,000,339 teaches that a silica-based compound, having improved oxygen plasma-resistance, improved physical properties and thickness of a coating film, can be obtained from the reaction of a monomer selected from the group consisting of alkoxysilane, fluorine-containing alkoxysilane and alkylalkoxysilane and a titanium- or zirconium-alkoxide compound in the presence of water and an appropriate catalyst. U.S. Pat. No. 5,853,808 discloses that siloxane- and silsesquioxane-based polymers useful for producing $SiO_2$-rich ceramic coatings can be obtained from hydrolysis and polycondensation of organosilanes possessing a β-substituted alkyl group. On the other hand, EP 0 997 497 A1 discloses that hydrolysis and polycondensation of a certain combination of alkoxysilanes including mono-, di-, tri- and tetra-alkoxysilanes as well as trialkoxysilane dimers can provide useful insulating materials. Meanwhile, U.S. Pat. No. 5,378,790 discloses inorganic/organic hybrid materials of excellent physical properties. U.S. Pat. No. 6,660,822 discloses a siloxane-based resin composition obtained from hydrolysis and polycondensation of circular siloxane monomers and a thin dielectric film produced therefrom.

However, dielectric films produced using those prior siloxane-based resins cannot achieve a satisfactory low dielectric constant, or they are deficient in mechanical properties and contain excessive carbon even though having a low dielectric constant. In particular, polymers prepared from a Si compound of Q structure, such as tetramethoxysilane, have good mechanical properties, but their high dielectric constant, due to inherent strong hygroscopicity, inhibit their use in the production of dielectric films, more particularly in the production of dielectric films through the SOD process. Recently, siloxane-based resins are required to have a good compatibility with pore-generating materials usually used for the purpose of further lowering the insulating coefficient thereof.

Consequently, there is a necessity for developing novel insulating materials that can be applied to a SOD process to produce dielectric films having a low insulating coefficient and good mechanical properties and which are compatible with pore-generating materials.

SUMMARY OF THE INVENTION

A feature of the present invention is to provide a multi-functional siloxane compound having improved reactivity which forms a ladder or network structure when polymerized.

Another feature of the present invention is to provided siloxane-based polymers and copolymers prepared from multi-functional siloxane compounds of a particular structure, the polymers and copolymers having excellent mechanical properties, thermal stability, crack-resistance, and low hygroscopicity, even under a SOG (Spin On Glass) process and good compatibility with pore generating material.

Still another feature of the present invention is to provide a process of producing a dielectric film using the siloxane-based polymer or copolymer.

In accordance with a feature of the present invention, there is provided a multi-functional cyclic siloxane compound (A) of formula (1a), below:

(1a)

wherein, $R_1$ is a hydrogen atom, a $C_{1-3}$ alkyl group or a $C_{6-15}$ aryl group;

$R_2$ is a $C_{1-10}$ alkyl group or $SiX_1X_2X_3$ (wherein, each of $X_1$, $X_2$ and $X_3$ is, independently, a hydrogen atom, a $C_{1-3}$ alkyl group, a $C_{1-10}$ alkoxy group or a halogen atom); and p is an integer from 3 to 8.

In accordance with another feature of the present invention, there is provided a siloxane-based polymer prepared by hydrolyzing and polycondensing the multi-functional cyclic siloxane compound (A) of formula (1) alone, or in combination with at least one monomer selected from the group consisting of compounds of formulas (2)-(5), in an organic solvent in the presence of an acid or base catalyst and water:

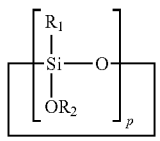  (1)

wherein, is a hydrogen atom, a $C_{1-3}$ alkyl group or a $C_{6-15}$ aryl group;

$R_2$ is a hydrogen atom, a $C_{1-10}$ alkyl group or $SiX_1X_2X_3$ (wherein, each of $X_1$, $X_2$ and $X_3$ is, independently, a hydrogen atom, a $C_{1-3}$ alkyl group, a $C_{1-10}$ alkoxy group or a halogen atom, provided that at least one of them is hydrolysable); and p is an integer from 3 to 8,

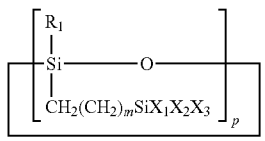  (2)

wherein, is a hydrogen atom, a $C_{1-3}$ alkyl group or a $C_{6-15}$ aryl group;

each of $X_1$, $X_2$ and $X_3$ is, independently, a hydrogen atom, a $C_{1-3}$ alkyl group, a $C_{1-10}$ alkoxy group or a halogen atom, provided that at least one of them is hydrolysable;

m is an integer from 0 to 10; and p is an integer from 3 to 8,

  (3)

wherein, each of $X_1$, $X_2$ and $X_3$ is, independently, a hydrogen atom, a $C_{1-3}$ alkyl group, a $C_{1-10}$ alkoxy group or a halogen atom, provided that at least one of them is hydrolysable; and M is a $C_{1-10}$ single bond, an alkylene group, or a $C_{6-15}$ arylene group, and

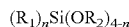  (4)

wherein, $R_1$ is a hydrogen atom, a $C_{1-3}$ an alkyl group, a $C_{6-15}$ aryl group or a halogen atom;

$R_2$ is a hydrogen atom, a $C_{1-3}$ alkyl group or a $C_{6-15}$ aryl group, provided that at least one of $R_1$ and $OR_2$ is hydrolysable; and

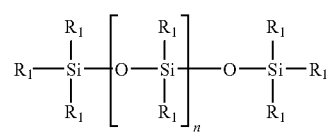  (5)

n is an integer from 0 to 3.

wherein, each of R1 is a hydrogen atom, a $C_{1-3}$ alkyl group, a $C_{1-10}$ alkoxy group, hydroxy or a halogen atom, provided that at least one of them is hydrolysable; and n is an integer from 0 to 30.

In accordance with still another-feature of the present invention, there is provided a process of producing an interlayer dielectric film of a semiconductor, the process comprising the steps of: (i) providing a liquid coating composition by dissolving the above siloxane-based polymer optionally with a pore-generating material in an organic solvent; and (ii) coating the liquid coating composition on a substrate and heat-curing the coated film.

In accordance with still another feature of the present invention, there is provided a dielectric film produced by the above process.

All of the above features and other features of the present invention will be successfully achieved from the present invention described in the following.

DETAILED DESCRIPTION OF THE INVENTION

Hereinafter, the present invention will be described in more detail.

Multi-Functional Cyclic Siloxane Compound (A)

The siloxane compound of the present invention represented by the formula (1a) below can form a ladder-like structure or other rigid structure in polymerization so that the polymer obtained from the siloxane compound has high mechanical properties, although the structure of the polymer obtained can not be predicted because of its random growth during polymerization:

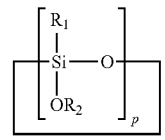  (1a)

wherein, $R_1$ is a hydrogen atom, a $C_{1-3}$ alkyl group or a $C_{6-15}$ aryl group;

$R_2$ is a $C_{1-3}$ alkyl group or a $SiX_1X_2X_3$ (wherein, each of $X_1$, $X_2$ and $X_3$ is, independently, a hydrogen atom, a $C_{1-3}$ alkyl group, a $C_{1-10}$ alkoxy group or a halogen atom); and p is an integer from 3 to 8.

Especially, if $R_2$ is $SiX_1X_2X_3$, wherein each of $X_1$, $X_2$ and $X_3$ is a $C_{1-10}$ alkoxy group, a Q structure in which Si in $R_2$ is connected to four oxygens, and a T structure in which Si of main chain is connected to oxygens, are formed simultaneously. In this case, the above monomer has very high reactivity and can form a rigid structure, so that the polymer prepared from the monomer has excellent mechanical properties. Because all of Si are linked with oxygen, it is possible to enhance the elasticity and porosity, in spite of the very low content of carbon. On the other hand, a general polymer prepared from a Si compound having the Q structure has a problem of an increase in the dielectric constant resulting from high hygroscopicity though it has good mechanical properties. But the siloxane compound according to the present invention is able to maintain low hygroscopicity and is excellent in its dielectric property when the Q structure is present in the compound. And the polymer prepared from this compound can have multiple Si—OH groups, so that it has excellent compatibility with conventional pore-generating materials.

A preferable example of the cyclic siloxane compound (A) of the present invention can be represented by the following formula (6), which corresponds to the above formula (1a) wherein $R_1$ is a methyl group, $R_2$ is $Si(OCH_3)_3$ and p is 4; the following formula (7), which corresponds to the above formula (1a) wherein $R_1$ is a methyl group, $R_2$ is H and p is 4; the following formula (8), which corresponds to the above formula (1a) wherein each of $R_1$ and $R_2$ is a methyl group and p is 4; the following formula (9), which corresponds to the above formula (1a) wherein $R_1$ is a methyl group, $R_2$ is $SiCH_3(OCH_3)_2$ and p is 4: the following formula (10), which corresponds to the above formula (1a) wherein $R_1$ is a methyl group, $R_2$ is $Si(CH_3)_2(OCH_3)$ and p is 4: or the following formula (11), which corresponds to the above formula (1a) wherein $R_1$ is methyl group, $R_2$ is $Si(CH_3)_3$ and p is 4:

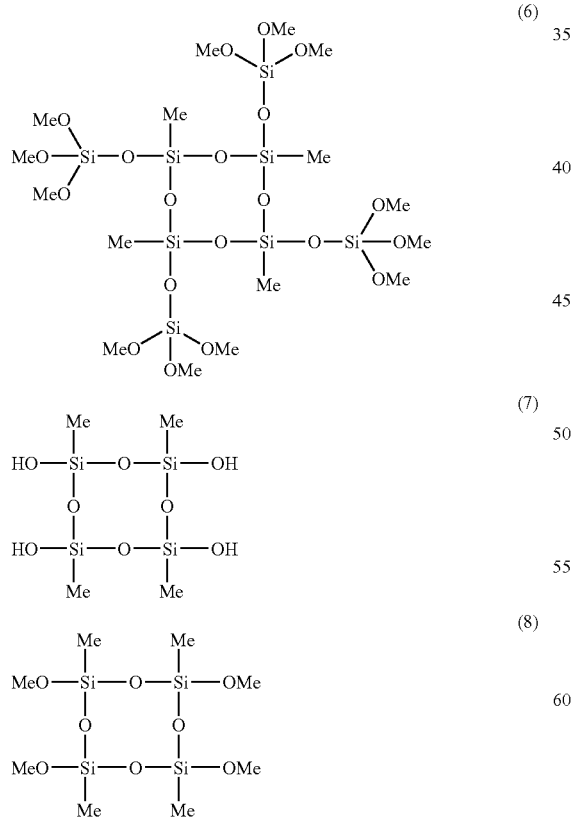

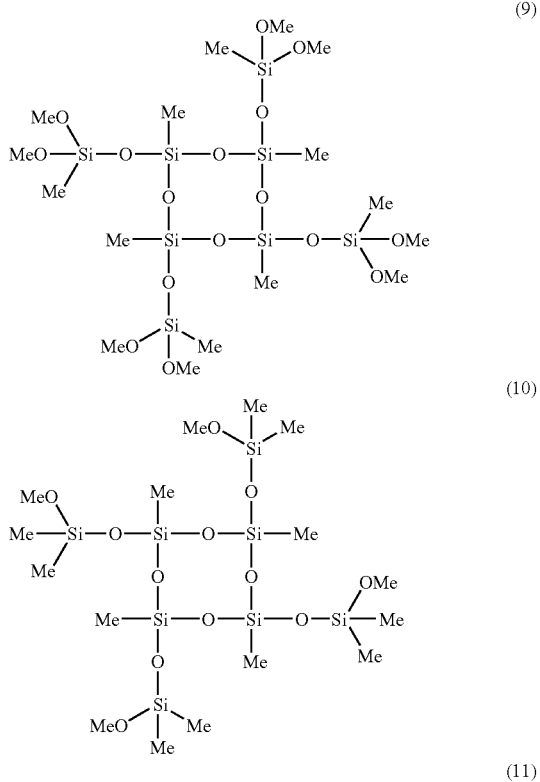

When $R_2$ is $SiX_1X_2X_3$ and all of $X_1$, $X_2$ and $X_3$ are alkoxy groups in the cyclic siloxane compound of the present invention, each Si in $R_2$ forms a Q structure as in tetramethoxysilane (TMOS) of the following formula (12):

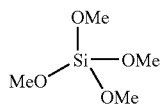

Accordingly, 1 mol of the compound of the formula (6) has an effect equivalent to 4 mol of TMOS, and the polymerization of the compound can yield a polymer significantly improved in mechanical properties. Furthermore, the compound of the formula (6) has such a lower hygroscopicity than TMOS as to be applied to a SOG process, while TMOS cannot be applied to a SOG process due to high hygroscopicity.

Siloxane-Based Polymer

The present invention provides a siloxane-based polymer which can be obtained by hydrolyzing and polycondensing the multi-functional cyclic siloxane compound (A) of the formula (1) in an organic solvent in the presence of an acid or base catalyst and water. As described above, the multi-functional cyclic siloxane compound has multiple reacting groups, so that the polymer obtained from this compound may have a ladder-like structure or network. Accordingly, the polymer can have excellent mechanical properties and maintains a low carbon content. A homopolymer can be prepared by using one multi-functional cyclic siloxane (A) as a monomer, or a copolymer can be prepared by polycondensing two or more siloxane compounds (A) such as a compound containing a Q structure in the terminal (e.g. the compound of formula 6), a compound containing a T structure (e.g. the compound of formula 9) and a compound containing a D structure (e.g. the compound of formula 10).

According to the present invention, there is provided a siloxane-based copolymer prepared by hydrolyzing and polycondensing the multi-functional cyclic siloxane compound (A) of formula (1) in combination with at least one monomer selected from the group consisting of Si monomers (B) having organic bridges represented by formulas (2)-(3), acyclic alkoxy silane monomers (C) represented by formula (4), and linear siloxane monomers (D) represented by formula (5) in an organic solvent in the presence of an acid or base catalyst and water:

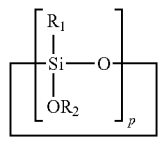
(1)

wherein, is a hydrogen atom, a $C_{1-3}$ alkyl group or a $C_{6-15}$ aryl group;

$R_2$ is a hydrogen atom, a $C_{1-10}$ alkyl group or $SiX_1X_2X_3$ (wherein, each of $X_1$, $X_2$ and $X_3$ is, independently, a hydrogen atom, a $C_{1-3}$ alkyl group, a $C_{1-10}$ alkoxy group or a halogen atom, provided that at least one of them is hydrolysable; and p is an integer from 3 to 8,

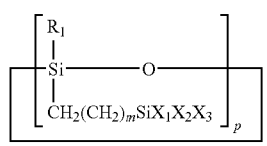
(2)

wherein, is a hydrogen atom, a $C_{1-3}$ alkyl group or a $C_{6-15}$ aryl group;

each of $X_1$, $X_2$ and $X_3$ is, independently, a hydrogen atom, a $C_{1-3}$ alkyl group, a $C_{1-10}$ alkoxy group or a halogen atom, provided that at least one of them is hydrolysable;

m is an integer from 0 to 10; and p is an integer from 3 to 8,

(3)

wherein, each of $X_1$, $X_2$ and $X_3$ is, independently, a hydrogen atom, a $C_{1-3}$ alkyl group, a $C_{1-10}$ alkoxy group or a halogen atom, provided that at least one of them is hydrolysable; and M is a single bond, a $C_{1-10}$ alkylene group, or a $C_{6-15}$ arylene group,

(4)

wherein, $R_1$ is a hydrogen atom, a $C_{1-3}$ alkyl group, a $C_{6-15}$ aryl group or a halogen atom;

$R_2$ is a hydrogen atom, a $C_{1-3}$ alkyl group or a $C_{6-15}$ aryl group, provided that at least one of $R_1$ and $OR_2$ is hydrolysable; and n is an integer from 0 to 3, and

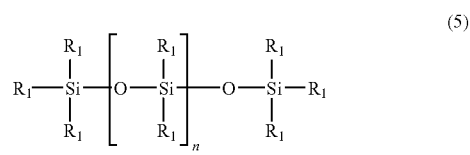
(5)

wherein, each of R1 is a hydrogen atom, a $C_{1-3}$ alkyl group, a $C_{1-10}$ alkoxy group, hydroxy or a halogen atom, provided that at least one of them is hydrolysable; and n is an integer from 0 to 30.

Preferably, the Si monomers of formulas (2) and (3) having organic bridges can be exemplified by the compounds of formulas (13)-(15) below:

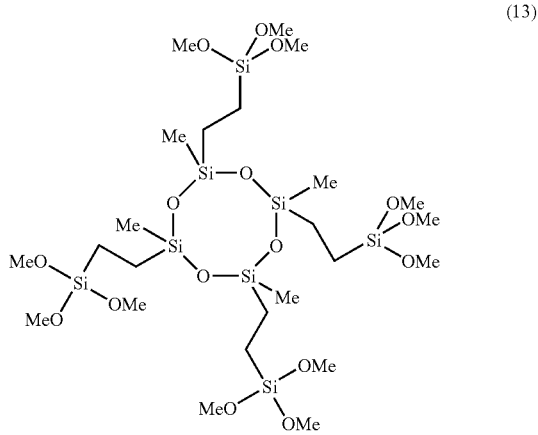
(13)

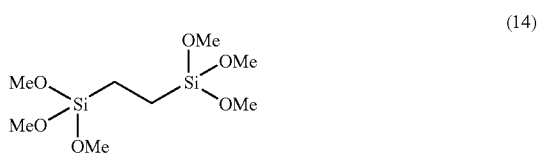
(14)

(15)

Also, preferable examples of the compound of formula (4) can include the compound of the above formula (12) and formulas (16)-(17) below:

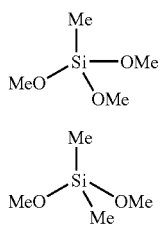

Also, preferable examples of the compound of formula (5) can include the compounds of formulas (18)-(22) below:

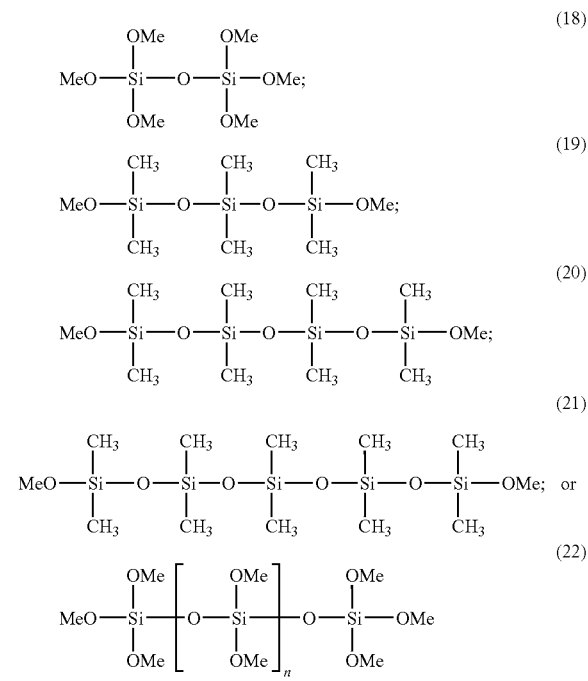

wherein, n is an integer from 0 to 30.

In case of copolymerizing the multi-functional cyclic siloxane compound (A) with at least one of the monomers of formula (2), (3), (4) and (5), the resulting copolymer can be evenly mixed with a pore-generating material because of the hydrolysable reacting group (for example, Si—OH or Si—OMe) contained in the monomer of formula (2), (3), (4) or (5). Further, the formation of a network by crosslinking proceeds favorably to provide a dielectric film of predominant mechanical properties including tensile strength and modulus. Additionally, the monomer of formulas (2) and (3) contains organic bridges, which produce vacant spaces in the course of polymerization, and therefore, the resulting copolymers have high elasticity as well as significantly increased molecular porosity conferring excellent insulating properties on the copolymer [*Journal of Sol-Gel Science and Technology,* 1997, 8, 541]. In this case, also, cyclic siloxane-based compound (A) of the present invention enhance the content of $SiO_2$ in the polymers so that the problems (for example, the difficulty in application to the line formation of a semiconductor and the double damascene process) in the case of using only monomer (B) can be solved. In addition, the polymers thus obtained can have a ladder-like structure therein and show excellent properties. On the other hand, if the Si monomer (B) having organic bridges is copolymerized, it is easy to control the rate of polymerization. Also, obtainable are molecular weight increases so that it is easy to establish the conditions of polymerization.

Also, if the cyclic siloxane compound (A) is copolymerized with the alkoxy silane monomer (C), or linear siloxane monomer (D), excellent mechanical properties and low hygroscopicity are obtained so that it can be possible to decrease the necessary content of pore-generating material in order to ensure a low dielectric constant.

In the case where the cyclic siloxane compound (A) is copolymerized with comonomer (B) and/or (C), (D), the molar ratio of the monomers is not specifically limited but determined depending on the required properties of a final dielectric film. For example, in case of copolymerizing the cyclic siloxane compound (A) of formula (1) with the comonomer (B), (C) or (D), the molar ratio of the former and the latter may range from 0.01:99.99 to 99.99:0.01.

Preferred organic solvents used in the preparation of the siloxane-based polymers of the present invention can be exemplified by, but are not limited to, aliphatic hydrocarbon solvents such as hexane and heptane; aromatic hydrocarbon solvents such as anisol, mesitylene and xylene; ketone-based solvents such as methyl isobutyl ketone, 1-methyl-2-pyrrolidinone, cyclohexanone and acetone; ether-based solvents such as tetrahydrofuran and isopropyl ether; acetate-based solvents such as ethyl acetate, butyl acetate and propylene glycol methyl ether acetate; alcohol-based solvents such as isopropyl alcohol and butyl alcohol; amide-based solvents such as dimethylacetamide and dimethylformamide; silicon-based solvents; and mixtures thereof.

Non-limiting examples of the catalyst used in the preparation of the siloxane-based polymers of the present invention include every known acid and alkali catalysts available for the preparation of polysilsesquioxanes, while hydrochloric acid, nitric acid, benzene sulfonic acid, oxalic acid and formic acid are preferred as the acid catalyst and potassium hydroxide, sodium hydroxide, triethylamine, sodium bicarbonate and pyridine are preferred as the alkali catalyst.

When preparing the siloxane-based polymers of the present invention, the molar ratio of the total monomers to be polymerized and the catalyst should ranges from $1:1\times10^{-5}$ to 1:10, and that of total monomers to be polymerized and water should ranges from 1:1 to 1:100.

According to the present invention, the reaction temperature, the time of hydrolysis and the polycondensation can be controlled appropriately, but they are preferably performed at 0-200° C. for 0.1-100 hrs.

Preferably, the siloxane-based polymers thus prepared have a Mw of 3,000-300,000, and the Si—OH content of total terminal groups is 5 mol % or more.

Process of Producing a Dielectric Film

The present invention further provides a process of producing a dielectric film, the process comprising the steps of: (i) providing a liquid coating composition by dissolving the inventive siloxane-based polymer in an organic solvent, optionally along with a pore-generating material; and (ii) applying the liquid coating composition to a substrate and heat-curing.

In the present invention, any of known pore-generating materials available for the preparation of a porous dielectric film can be used. Preferably, one or more pore-generating materials can be used which are selected from the group consisting of cyclodextrin, polycaprolactone, Brij-based surfactant, polyethyleneglycol-polypropyleneglycol-polyethyleneglycol triblock copolymer surfactant, and derivatives thereof. The pore-generating material content of the liquid coating composition is preferably 0-70 wt % based on total weight of the solid matter (inclusive of the siloxane-base polymer and the pore-generating material) in the composition.

The organic solvent used in the preparation of the liquid coating composition is not specifically limited but can be one or more selected from those described above as polymerization solvents. The solid matter content of the liquid coating composition is not specifically limited but is preferably 5-70 wt % based on total weight of the composition.

In the present invention, the substrate is not specifically limited and any known substrate such as a glass substrate, a silicon wafer and a plastic substrate can be used according to the desired use. Non-limiting examples of the method of applying the liquid coating composition to a substrate include spin-coating, dip-coating, spray-coating, flow-coating and screen-printing, while spin-coating is most preferred in consideration of convenience and evenness. For spin-coating, the spin rate is controlled to fall between 800 and 5,000 rpm.

At the completion of the coating, the resulting coating film may be dried by evaporating the organic solvent. This film-drying step can be carried out by exposing the coated substrate to an environmental atmosphere or to a vacuum condition at the beginning of the subsequent heat-curing step or to mild heating at 200° C. or less.

Subsequently, the coating film is cured by heating at 150-600° C., preferably at 200-450° C. for 1-180 minutes so as to provide an insoluble, crack-free film. As used herein, by "crack-free film" is meant a film without any crack observed with an optical microscope at a magnification of 1000×. As used herein, by "insoluble film" is meant a film substantially insoluble in any solvent described as being useful for the preparation of the liquid coating composition.

A dielectric film consisting of only the siloxane-based polymer of the present invention has a low dielectric constant of 3.0 or less and thus it can be used as an interlayer low dielectric coating film of a semiconductor. A dielectric film prepared using the siloxane-based polymer of the present invention and the pore-generating material has a dielectric constant of 2.5 or less. The dielectric films produced according to the present invention are excellent in mechanical properties such as tensile strength and elasticity and furthermore have low carbon content, so they are useful as an interlayer dielectric film of a semiconductor.

The present invention can be more clearly understood by referring to the following examples. It should be understood that the following examples are not intended to restrict the scope of the present invention in any manner.

EXAMPLES

Evaluation of properties of the dielectric films obtained from the following examples is performed as follows:
1) Dielectric Constant
A P-type silicon wafer doped with boron is coated with a 3000 Å of thermally-oxidized silicon film, followed by the sequential deposition of a 100 Å of titanium layer, a 2000 Å of aluminum layer and a 100 Å of titanium layer using a metal evaporator. On the top of the metal layer is formed a dielectric film to be evaluated. Subsequently, on the dielectric film is deposited a circular electrode having a diameter of 1 mm in diameter by the use of a hard mask, the electrode consisting of a 100 Å of titanium layer and a 5000 Å of aluminum layer, so as to provide a test piece of a MIM (metal-insulator-metal) structure.

The test piece thus prepared is subjected to the measurement of capacitance at frequency of 10 kHz, 100 kHz and 1 MHz using PRECISION LCR METER (HP4284A) with Micromanipulator 6200 probe station. Dielectric constant of the inventive dielectric film is calculated from the following equation, wherein "d" value was obtained by the use of a prism coupler:

$$k=(C \times d)/(\epsilon_o \times A)$$

Note)
k: relative permittivity
C: capacitance
$\epsilon_o$: dielectric constant in vacuum ($\epsilon_o = 8.8542 \times 10^{-12}$ Fm$^{-1}$)
d: thickness of the dielectric film
A: contact area of the electrode
2) Hardness and Elastic Modulus
The hardness and elastic modulus of the inventive dielectric film are determined by the use of Nanoindenter II (MTS Co.). At this time, the indentation of the dielectric film is performed until the indentation depth reached 10% of its entire thickness. The thickness of the dielectric film is previously measured by the use of a prism coupler. In the present invention, to guarantee the reliability of the measurement, 9 points are indented every test piece and then mean hardness and modulus are taken.
3) Carbon Content
The carbon content of the inventive dielectric film is determined using XPS (X-ray photoelectron spectroscopy) which is determined by Q 2000 (Physical Electronics Co.). At this time, monochromatic Al source (1486.6 eV) is used for X-ray generating. Sputtering is performed by the use of 3 keV Ar ion, and the quantitative element analysis according to depth was performed. Mean carbon content is taken from an area over which content of each element is consistent.

Synthesis of a Multi-Functional Cyclic Siloxane Monomer (A)

Synthesis Example 1

Synthesis of Monomer (A-1)

To a flask is introduced 10.00 g (41.6 mmol) of 2,4,6,8-tetramethyl-2,4,6,8-cyclotetrasiloxane and diluted with 100 ml of THF (tetrahydrofuran). To the solution is added 700 mg of 10 wt % Pd/C (palladium/charcoal) and 3.20 ml (177.8 mmol) of deionized water with removing hydrogen gas. Thereafter, the reaction is continued at room temperature for 15 hrs and then filtrated through celite and MgSO$_4$. From the filtrate are evaporated volatile substances under a reduced pressure of 0.1 torr to produce a concentrated liquid colorless monomer (A-1) of the following formula (7):

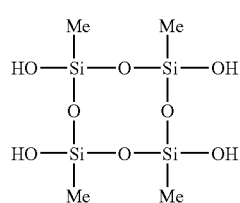

(7)

The results of the NMR analysis of the monomer thus obtained are as follows:
$^1$H-NMR (300 MHz, in acetone-d$_6$) δ 0.067 (s, 12H, 4×[—CH$_3$]), 5.52 (s, 4H, 4×[—OH]

Synthesis Example 2

Synthesis of Monomer (A-2)

With the exception that 2,4,6,8-tetramethyl-2,4,6,8-cyclotetrasiloxane is replaced with 2,4,6,8,10-pentamethyl-2,4,6,8,10-cyclopentasiloxane, the procedure of the Synthesis of Example 2 is performed in the same manner as in the Synthesis of Example 1 to produce a monomer (A-2) of the following formula:

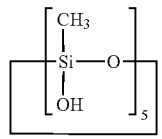

The results of the NMR analysis of the monomer (A-2) thus obtained are as follows:

$^1$H-NMR (300 MHz, in acetone-$d_6$): δ 0.092 (s, 15H, 5×[—CH$_3$]), 5.71 (s, 5H, 5×[—OH]).

Synthesis Example 3

Synthesis of Monomer (A-3)

To a flask is introduced 3.8 g (21.4 mmol) of PdCl$_2$(II) and dissolved in 50 ml of CCl$_4$. After slowly adding 10.00 g (41.6 mmol) of 2,4,6,8-tetramethyl-2,4,6,8-cyclotetrasiloxane to the solution, the reaction is continued at room temperature for 10 minutes, followed by filtration through celite and MgSO$_4$. After diluting the filtrate with 200 ml of THF (tetrahydrofuran), 18.5 g (183.0 mmol) of triethylamine is added thereto. The mixture is reacted at room temperature for 10 minutes, and an excess amount (11.7 g; 366.1 mmol) of methyl alcohol is added thereto, and the reaction is continued for 5 hours, followed by filtration through celite. From the filtrate are evaporated volatile substances under a reduced pressure of 0.1 torr to produce a concentrated liquid monomer of (A-3) of the following formula (8):

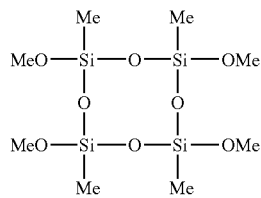

The results of the NMR analysis of the monomer (A-3) thus obtained are as follows:

$^1$H-NMR (300 MHz, in acetone-$d_6$): δ 0.067 (s, 12H, 4×[—CH$_3$]), 3.55 (s, 3H, 4×[—OCH$_3$]).

Synthesis Example 4

Synthesis of Monomer (A-4)

To a solution prepared by diluting 12.6 g (41.6 mmol) of the liquid monomer of formula (6) obtained from the above Synthesis Example 1 with 200 ml of THF is added 13.83 g (177.8 mmol) of triethylamine. After cooling the reaction mixture down to –0° C., 25.0 g (177.8 mmol) of chlorodimethoxymethylsilane is slowly added thereto. The reaction mixture is slowly warmed up to room temperature and then the reaction is continued for 12 hrs. At the completion of the reaction, the reaction mixture is filtrated through celite. From the filtrate are evaporated volatile substances under a reduced pressure of 0.1 torr to produce a concentrated liquid monomer (A-4) of the following formula (9):

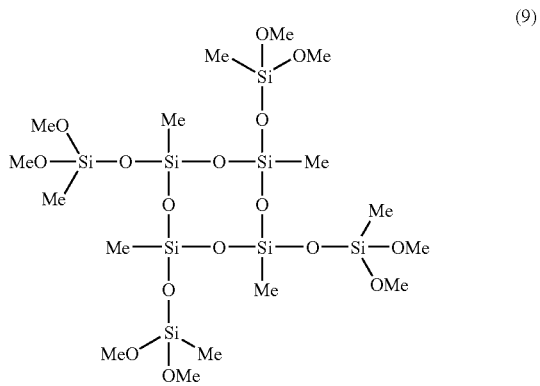

The results of NMR analysis of the monomer (A-4) thus obtained are as follows:

$^1$H-NMR (300 MHz, in acetone-$d_6$): δ 0.12 (s, 12H, 4×[—CH$_3$]), 0.24 (s, 12H, 4×[—CH$_3$]), 3.53 (s, 24H, 4×[—OCH$_3$]$_2$)

Synthesis Example 5

Synthesis of Monomer (A-5)

With the exception that chlorodimethoxymethylsilane is replaced with chlorotrimethoxysilane, the procedure of Synthesis Example 5 is performed in the same manner as in the Synthesis of Example 4 to produce monomer (A-5) of the following formula (6):

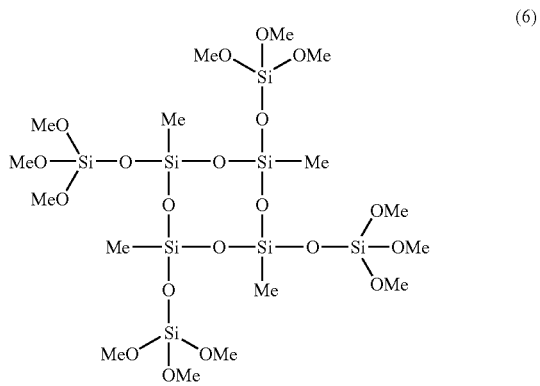

The results of NMR analysis of the monomer (A-5) thus obtained are as follows:

$^1$H-NMR (300 MHz, in acetone-dr): δ 0.092 (s, 12H, 4×[—CH$_3$]), 3.58 (s, 36H, 4×[—OCH$_3$]$_3$).

Synthesis Example 6

Synthesis of Monomer (A-6)

With the exception that chlorodimethoxymethylsilane is replaced with chlorodimethylmethoxysilane, the procedure of Synthesis Example 6 is performed in the same manner as in the Synthesis of Example 4 to produce monomer (A-6) of the following formula (10):

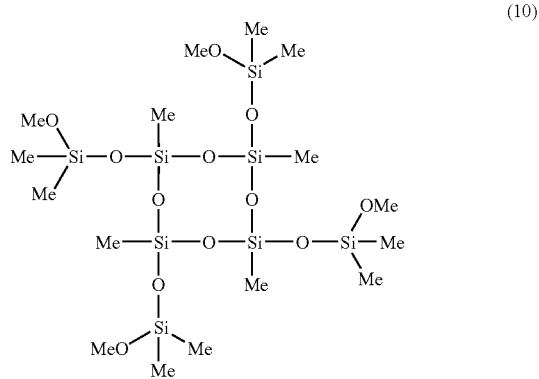

(10)

The results of NMR analysis of the monomer (A-6) thus obtained are as follows:

$^1$H-NMR (300 MHz, in acetone-$d_6$): δ 0.068 (s, 24H, 4×[—CH$_3$]$_2$), 0.092 (s, 12H, 4×[—CH$_3$]), 3.58 (s, 12H, 4×[—OCH$_3$]).

Synthesis Example 7

Synthesis of Monomer (A-7)

With the exception that chlorodimethoxymethylsilane is replaced with trimethylsilane, the procedure of Synthesis Example 7 is performed in the same manner as in the above Synthesis Example 4 to produce monomer (A-7) of the following formula (11):

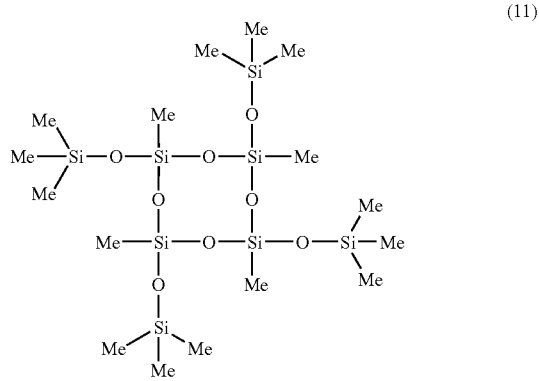

(11)

The results of NMR analysis of the monomer (A-7) thus obtained are as follows:

$^1$H-NMR (300 MHz, in acetone-$d_6$): δ 0.059 (s, 36H, 4×[—CH$_3$]$_3$), 0.092 (s, 12H, 4×[—CH$_3$]).

Synthesis of Monomer (B)

To a flask are introduced 10.0 g (29.01 mmol) of 2,4,6,8-tetramethyl-2,4,6,8-tetravinylcyclotetrasiloxane and 0.164 g of platinum(O)-1,3-divinyl-1,1,3,3-tetramethyldisiloxane complex solution in xylene and diluted with 300 ml of diethylether. After cooling the reaction mixture down to −78° C., 17.29 g (127.66 mmol) of trichlorosilane is slowly added thereto. At the completion of the addition, the reaction mixture is slowly warmed up to room temperature. The reaction is continued at room temperature for 40 hrs, and volatile substances are removed from the reaction mixture under a reduced pressure of about 0.1 torr to produce a concentrate. Subsequently, to the concentrate is added 100 ml of hexane and stirred for 1 hr, followed by filtration through celite. From the filtrate is evaporated hexane under a reduced pressure of about 0.1 torr to produce a liquid product.

10.0 g (11.56 mmol) of the liquid product obtained above is diluted with 50 ml of THF (tetrahydrofuran), and 13.83 g (136.71 mmol) of triethylamine is added thereto. After cooling the reaction mixture down to −78° C., 4.38 g (136.71 mmol) of methyl alcohol is slowly added thereto. At the completion of the addition, the reaction mixture is slowly warmed up to room temperature. The reaction is continued at room temperature for 15 hrs and filtered through celite. Then volatile substances are evaporated from the filtrate under a reduced pressure of about 0.1 torr to produce a concentrate. To the concentrate is added 100 ml of hexane and stirred for 1 hr, followed by filtration through celite. To the filtrate is added 5 g of activated carbon and stirred for 10 hrs, followed by filtration through celite. From the filtrate is evaporated hexane under a reduced pressure of about 0.1 torr to produce a concentrated liquid colorless monomer (B) of the following formula (13):

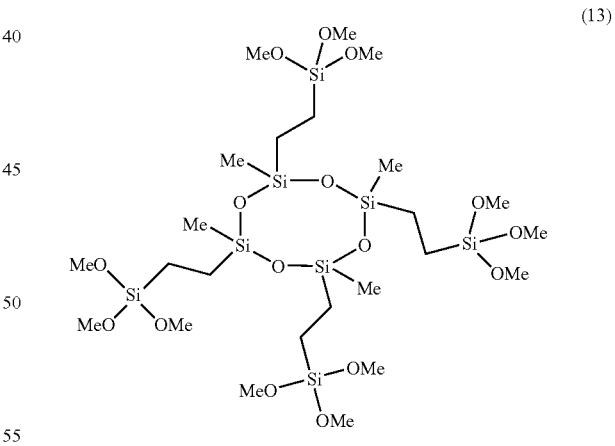

(13)

The results of NMR analysis of the monomer (B) thus obtained are as follows:

$^1$H-NMR (300 MHz, in acetone-$d_6$): δ 0.09 (s, 12H, 4×[—CH$_3$]), 0.52~0.64 (m, 16H, 4×[—CH$_2$CH$_2$—]), 3.58 (s, 36H, 4×[—OCH$_3$]$_3$).

Synthesis of Monomer (D)

To a flask are introduced 2.8 g (9.83 mmol) of hexaclorodisiloxane diluted with 150 ml of Methanol. 7.94 g (78.64 mmol) of triethyl amine is slowly added thereto. The reaction is continued at room temperature for 2 hrs, and filtered through celite. Then volatile substances are evaporated from the filtrate under a reduced pressure of about 0.1 torr to produce a concentrate. To the concentrate is added 100 ml of hexane and stirred for 1 hr, followed by filtration through celite. From the filtrate is evaporated hexane under a reduced pressure of about 0.1 torr to produce a concentrated liquid colorless monomer (D) of the following formula (18):

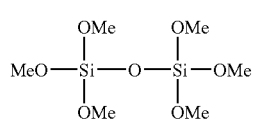
(18)

The results of NMR analysis of the monomer (18) thus obtained are as follows:

$^1$H-NMR (300 MHz, in acetone-$d_6$): δ 3.58 (s, 18H, 6×[—OCH$_3$]).

Production of Copolymer (a)

The multi-functional cyclic siloxane-based monomer (A-1)(8.24 mmol) and (A-5) (3.53 mmol) are introduced to a flask, followed by dilution with THF so that final concentration of the solution could range from 0.05 to 0.07M. Subsequently, the solution is cooled down to −78° C., and 0.424 mmol of HCl and 141.2 mmol of deionized water are slowly added thereto. Then the reaction mixture is slowly warmed up to 70° C. The reaction is continued for 16 hrs and transferred to a separatory funnel. To the separatory funnel is introduced the reaction mixture with the same volume of diethylether and THF as that of THF used in the dilution of the monomers at the beginning of the reaction. After washing the reaction mixture with 1/10× volume of deionized water, volatile substances are evaporated from it under reduced pressure to produce a white powdery polymer. The powdery polymer is dissolved in acetone to afford a clear solution, followed by filtration through a 0.2 μm syringe filter. To the filtrate is slowly added water to precipitate white powder. The white $^1$H-NMR (300 MHz, in acetone-$d_6$): δ 0.059 (s, 36H, 4×[—CH$_3$]$_3$), 0.092 (s, 12H, 4×[—CH$_3$]). powder is recovered and dried at 0-20° C. under a reduced pressure of 0.1 torr for 10 hrs to produce desired siloxane-based polymers.

Si—OH, Si—OCH$_3$ and Si—CH$_3$ content (%) of the polymers, determined by the use of a NMR device (Bruker Co.) and the following equations, is also presented:

Si—OH (%)=Area(Si—OH)×[Area(Si—OH)+Area(Si—OCH$_3$)/3+Area(Si—CH$_3$)/3]×100;

Si—OCH$_3$(%)=Area(Si—OCH$_3$)/3÷[Area(Si—OH)+Area(Si—OCH$_3$)/3+Area(Si—CH$_3$)/3]×100; and, Si—CH$_3$(%)=Area(Si—CH$_3$)/3÷[Area(Si—OH)+Area(Si—OCH$_3$)/3+Area(Si—CH$_3$)/3]×100.

Production of Copolymers (b) to (d)

Polymers (b), (c) and (d) are produced according to the same manner as in the production of polymer (a), except that monomer (A-5) is replaced with the compound represented by formula (13) as a Si monomer having organic bridges and HCl and water are used in the amounts as described in Table 1 below. The amount of the polymer thus obtained is shown in Table 1 along with the Si—OH, Si—OCH$_3$ and Si—CH$_3$ content (%) thereof.

TABLE 1

| Polymer | Monomer (mmol) (A-1) | Monomer (mmol) (B) | HCl (mmol) | H$_2$O (mmol) | Polymer (g) | Si—OH (%) | Si—OCH$_3$ (%) | Si—CH$_3$ (%) |
|---|---|---|---|---|---|---|---|---|
| (b) | 2.04 | 8.16 | 0.098 | 326.4 | 5.20 | 33.31 | 1.43 | 65.26 |
| (c) | 8.31 | 8.31 | 0.100 | 332.4 | 4.90 | 25.57 | 1.10 | 73.33 |
| (d) | 20.69 | 2.30 | 0.028 | 92.0 | 3.40 | 26.14 | 3.95 | 69.91 |

Production of Polymers (e) to (g)

Polymers (e), (f) and (g) are produced according to the same manner as in the production of polymer (a), except that monomer (A-5) is replaced with 1,2-bis(trimethoxysilyl)ethane (BTMSE; Aldrich) as a Si monomer having organic bridges and HCl and water are used in the amounts as described in Table 2 below. The amount of the polymer thus obtained is shown in Table 2 along with Si—OH, Si—OCH$_3$ and Si—CH$_3$ content (%) thereof.

TABLE 2

| Polymer | Monomer (mmol) (A-1) | Monomer (mmol) BTMSE | HCl (mmol) | H$_2$O (mmol) | Polymer (g) | Si—OH (%) | Si—OCH$_3$ (%) | Si—CH$_3$ (%) |
|---|---|---|---|---|---|---|---|---|
| (e) | 2.04 | 8.16 | 0.049 | 163.2 | 1.80 | 19.24 | 1.32 | 79.44 |
| (f) | 8.31 | 8.31 | 0.050 | 166.2 | 1.60 | 16.55 | 1.25 | 82.20 |
| (g) | 20.69 | 2.30 | 0.014 | 46.0 | 1.60 | 15.68 | 1.10 | 83.22 |

Production of Polymer (h)

Polymer (h) is produced according to the same manner as in the production of polymer (a), except that 5.09 mmol of monomer (A-5) and 11.88 mmol of 1,2-bis(trimethoxysilyl) ethane) (BTMSE; Aldrich) as a Si monomer having organic bridges are used. And 1.324 mmol of HCl and 441.2 mmol of water are used. As a result, 3.90 g of polymer is obtained, and Si—OH, Si—OCH$_3$ and Si—CH$_3$ content (%) thereof is, respectively, 27.50%, 0.92% and 71.58%.

Production of Polymers (i) to (m)

Polymers (i), (j), (k), (l) and (m) are produced in the same manner as in the production of polymer (a), except that monomer (A-5) and methyltrimethoxysilane (MTMS, Aldrich) as an acyclic alkoxy silane monomer are used, and HCl and water are used in the amounts as described in Table 3 below. The amount of the polymer thus obtained is shown in Table 3 along with Si—OH, Si—OCH$_3$ and Si—CH$_3$ content (%) thereof.

TABLE 3

| Polymer | Monomer (mmol) | | HCl (mmol) | H$_2$O (mmol) | Polymer (g) | Si—OH (%) | Si—OCH$_3$ (%) | Si—CH$_3$ (%) |
|---|---|---|---|---|---|---|---|---|
| | (A-5) | MTMS | | | | | | |
| (i) | 2.55 | 124.95 | 4.055 | 1351.4 | 2.30 | 21.80 | 0.60 | 77.50 |
| (j) | 3.82 | 72.58 | 2.636 | 878.5 | 3.40 | 25.40 | 0.80 | 73.80 |
| (k) | 5.09 | 45.81 | 1.985 | 661.6 | 4.40 | 28.20 | 0.90 | 70.90 |
| (l) | 5.09 | 28.84 | 1.476 | 492.0 | 4.20 | 31.40 | 1.20 | 67.40 |
| (m) | 5.09 | 20.36 | 1.222 | 407.2 | 3.70 | 33.60 | 1.30 | 65.10 |

Production of Polymer (n)

Polymer (n) is produced according to the same manner as in the production of polymer (a), except that 20.69 mmol of monomer (A-3) and 2.30 mmol of the compound represented by formula (10) as the Si monomer having organic bridges are used. And 1.104 mmol of HCl and 367.8 mmol of water are also used. As a result 2.80 g of polymer is obtained, and Si—OH, Si—OCH$_3$ and Si—CH$_3$ content (%) thereof is, respectively, 29.91%, 1.09% and 72.00%.

Production of Polymer (o)

Polymer (o) is produced according to the same manner as in the production of polymer (a), except that 20.69 mmol of monomer (A-4) and 2.30 mmol of the compound represented by formula (13) as a Si monomer having organic bridges are used. And 1.932 mmol of HCl and 643.7 mmol of water are also used. As a result 3.60 g of polymer is obtained, and Si—OH, Si—OCH$_3$ and Si—CH$_3$ content (%) thereof is, respectively, 16.58%, 0.98% and 82.04%.

Production of Polymer (p) to (u)

Polymers (p), (q), (r), (s), (t) and (u) are produced in the same manner as in the production of polymer (a), except that monomer (A-5), monomer (A-5) and monomer (A-6) as a cyclic alkoxy silane monomer are used, and HCl and water are also used in the amounts as described in Table 3 below. The amount of the polymer thus obtained is shown in Table 3 along with Si—OH, Si—OCH$_3$ and Si—CH$_3$ content (%) thereof.

TABLE 3

| Polymer | Monomer (mmol) | | HCl (mmol) | H$_2$O (mmol) | Polymer (g) | Si—OH (%) | Si—OCH$_3$ (%) | Si—CH$_3$ (%) |
|---|---|---|---|---|---|---|---|---|
| | (A-5) | (A-4) | | | | | | |
| (p) | 10 | 0 | 4.055 | 1351.4 | 2.30 | 21.80 | 0.60 | 77.50 |
| (q) | 5 | 5 | 2.636 | 878.5 | 3.40 | 25.40 | 0.80 | 73.80 |
| (r) | 0 | 10 | 1.985 | 661.6 | 4.40 | 28.20 | 0.90 | 70.90 |
| | (A-5) | (A-6) | | | | | | |
| (s) | 5 | 5 | 1.476 | 492.0 | 4.20 | 31.40 | 1.20 | 67.40 |
| (t) | 0 | 10 | 1.222 | 407.2 | 3.70 | 33.60 | 1.30 | 65.10 |
| | (A-4) | (A-6) | | | | | | |
| (u) | 5 | 5 | 1.222 | 407.2 | 3.70 | 33.60 | 1.30 | 65.10 |

Production of Polymer (v)

Polymer (v) is produced according to the same manner as in the production of polymer (a), except that 5.09 mmol of monomer (A-5), and 20.36 mmol of dimethyldimethoxysilane (DMDMS; Aldrich) as a acyclic siloxane monomer are used. and 1.222 mmol of HCl and 407.2 mmol of water are also used. As a result, 3.40 g of polymer is obtained, and Si—OH, Si—OCH$_3$ and Si—CH$_3$ content (%) thereof is, respectively, 26.4%, 0.6% and 73.0%.

Production of Polymer (w)

Polymer (w) is produced according to the same manner as in the production of polymer (a), except that 4.07 mmol of monomer (A-5), 20.36 mmol of methyltrimethoxysilane (MTMS; Aldrich) and 2.71 mmol of hexamethoxydisiloxane (D) as a linear siloxane monomer are used. and 1.222 mmol of HCl and 407.2 mmol of water are used. As a result, 3.90 g of polymer is obtained, and Si—OH, Si—OCH$_3$ and Si—CH$_3$ content (%) thereof is, respectively, 32.0%, 0.6% and 67.4%.

Production of Polymer (x)

Polymer (x) is produced according to the same manner as in the production of polymer (a), except that 5.09 mmol of monomer (A-5), and 5.09 mmol of poly(methylhydrosiloxane) (mw=3174, Aldrich) as a acyclic siloxane monomer are used. and 0.611 mmol of HCl and 407.2 mmol of water are also used. As a result, 1.80 g of polymer is obtained, and Si—OH, Si—OCH$_3$ and Si—CH$_3$ content (%) thereof is, respectively, 23.5%, 0.6% and 75.9%.

Production of Polymer (y)

Polymer (y) is produced according to the same manner as in the production of polymer (a), except that 5.09 mmol of monomer (A-5), and 1.27 mmol of poly(methylhydrosiloxane) (mn=390, Aldrich) as a acyclic siloxane monomer are used. and 0.611 mmol of HCl and 407.2 mmol of water are also used. As a result, 1.65 g of polymer is obtained, and Si—OH, Si—OCH$_3$ and Si—CH$_3$ content (%) thereof is, respectively, 22.8%, 0.6% and 76.6%.

Production of Dielectric Film A and A-1

0.428 g of siloxane-based polymer (a) alone (dielectric film A), or 0.428 g of siloxane-based polymer (a) and 0.183 g of heptakis (2,3,6-tri-O-methoxy)-β-cyclodextrin (dielectric film A-1) as a pore-generating material are dissolved in PGMEA (propylene glycol methyl ether acetate) so that the final concentration of the solid matter (inclusive of the polymer and the pore-generating material) in the resulting liquid coating composition could amount to 30 wt %. The liquid coating composition is applied to a silicon wafer by spin-coating for 30 seconds while maintaining the spin rate of 3,000 rpm. Under a nitrogen atmosphere, the coated wafer is put on a hot plate and preheated for 1 minute at 150° C. and for another minute at 250° C. to produce a dried coating film. Under vacuum condition, the temperature of the coating film is elevated up to 420° C. at a rate of 3° C./min, where the film is subjected to heat-curing for 1 hr to produce dielectric films A and A-1. The dielectric films are analyzed for thickness, refractive index, dielectric constant, hardness, elastic modulus and carbon content, and the results are shown in Table 4 below.

Production of Dielectric Films B-D, I-N, P-U and W-X

Each of dielectric films B, B-1, C, C-1, D, D-1, I, I-1, J, J-1, K, K-1, L, L-1, M, M-1, N, N-1, P, P-1, Q, Q-1, R, R-1, S, S-1, T, T-1, U, U-1, W, W-1, X and X-1 are produced according to the same manner as in the production of dielectric films A or A-1, except that polymer (a) is replaced with polymers (b)-(d) and (i)-(n), (p)-(u) and (w)-(x), respectively. The dielectric films are analyzed for thickness, refractive index, dielectric constant, hardness, elastic modulus and carbon content, and the results are shown in Table 4 below.

TABLE 4

| Dielectric film | R.I.[1] | T[2] (Å) | D.C.[3] | H[4] (GPa) | E.M.[5] (Gpa) | C.C.[6] (%) |
|---|---|---|---|---|---|---|
| (A) | 1.388 | 14680 | 2.87 | 1.28 | 7.32 | 10.5 |
| (A-1) | 1.281 | 13200 | 2.25 | 0.52 | 3.18 | 8.30 |
| (B) | 1.436 | 9730 | 2.45 | 1.04 | 6.07 | 32.5 |
| (B-1) | 1.325 | 8430 | 2.10 | 0.45 | 3.15 | 29.1 |
| (C) | 1.418 | 11860 | 2.55 | 0.89 | 5.03 | 28.3 |
| (C-1) | 1.325 | 9760 | 2.17 | 0.42 | 2.90 | 25.2 |
| (D) | 1.400 | 7800 | 2.64 | 0.78 | 4.80 | 24.4 |
| (D-1) | 1.321 | 6790 | 2.20 | 0.37 | 2.75 | 22.2 |
| (I) | 1.378 | 8670 | 2.59 | 0.99 | 5.34 | 18.8 |
| (I-1) | 1.306 | 7140 | 2.35 | 0.57 | 3.24 | 15.3 |
| (J) | 1.381 | 8960 | 2.88 | 1.15 | 6.08 | 16.3 |
| (J-1) | 1.295 | 7140 | 2.30 | 0.56 | 3.32 | 13.6 |
| (K) | 1.383 | 9230 | 3.06 | 1.28 | 7.24 | 15.4 |
| (K-1) | 1.288 | 7730 | 2.28 | 0.50 | 3.08 | 11.1 |
| (L) | 1.385 | 6029 | 3.07 | 1.42 | 8.01 | 12.7 |
| (L-1) | 1.280 | 7915 | 2.07 | 0.55 | 3.22 | 9.4 |
| (M) | 1.397 | 6936 | 3.01 | 1.85 | 10.28 | 10.0 |
| (M-1) | 1.286 | 7099 | 2.09 | 0.71 | 4.15 | 7.9 |
| (N) | 1.402 | 11600 | 2.64 | 0.80 | 5.01 | 25.0 |
| (N-1) | 1.327 | 10900 | 2.24 | 0.39 | 2.92 | 22.5 |
| (P) | 1.385 | 7760 | 3.29 | 1.72 | 11.67 | 9.3 |
| (P-1) | 1.318 | 9740 | 2.60 | 0.95 | 6.64 | 7.2 |
| (Q) | 1.395 | 4920 | 2.50 | 1.45 | 8.48 | 11.7 |
| (Q-1) | 1.321 | 5640 | 2.02 | 0.37 | 3.95 | 10.1 |
| (R) | 1.401 | 3380 | 2.78 | 0.73 | 5.97 | 13.3 |
| (R-1) | 1.330 | 1840 | 2.45 | 0.66 | 4.00 | 11.6 |
| (S) | 1.379 | 3820 | 2.68 | 0.87 | 5.98 | 13.9 |
| (S-1) | 1.310 | 3900 | 1.85 | 0.58 | 3.92 | 12.0 |
| (T) | 1.377 | 3200 | 2.84 | 0.71 | 5.43 | 16.2 |
| (T-1) | 1.305 | 3800 | 2.38 | 0.35 | 3.68 | 13.9 |
| (U) | 1.381 | 2500 | 2.78 | 0.64 | 6.16 | 14.4 |
| (U-1) | 1.312 | 2900 | 2.21 | 0.30 | 3.69 | 11.8 |
| (W) | 1.387 | 9030 | 2.90 | 1.70 | 10.55 | 10.0 |
| (W-1) | 1.298 | 7660 | 2.30 | 0.70 | 4.50 | 8.2 |
| (X) | 1.377 | 6953 | 2.86 | 0.91 | 6.47 | 14.1 |
| (X-1) | 1.305 | 7469 | 2.41 | 0.65 | 3.91 | 12.5 |

[1] refractive index
[2] thickness
[3] dielectric constant
[4] hardness
[5] elastic modulus
[6] carbon content Although the preferred embodiments of the present invention have been disclosed for illustrative purposes, those skilled in the art will appreciate that various modifications, additions and substitutions are possible, without departing from the spirit and scope of the invention.

What is claimed is:

1. A multi-functional cyclic siloxane compound of formula (1a):

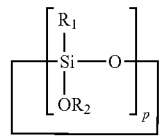

(1a)

wherein,

R1 is a hydrogen atom, a $C_{1-3}$ alkyl group or a $C_6$ aryl group; $R_2$ is $SiX_1X_2X_3$ (wherein, each of $X_1$, $X_2$ and $X_3$ is, independently, a hydrogen atom, a $C_{1-3}$ alkyl group, a $C_{1-10}$ alkoxy group or a halogen atom, provided that at least one X group is hydrolyzable, and p is an integer from 3 to 8.

2. A process of producing an interlayer dielectric film of a semiconductor, the process comprising the steps of: (i) providing a liquid coating composition by dissolving a sioxane-based polymer optionally with a pore-generating material in an organic solvent; and (ii) coating the liquid coating composition on a substrate and heat-curing the coated film, wherein the sioxane-based polymer having repeat units of a cyclic Si—O structure, is prepared by hydrolyzing and polycondensing at least one multi-functional cyclic sioxane compound of formula (1) alone, or in combination with at least one monomer selected from the group consisting of the compounds of formulas (2)-(5), in an organic solvent in the presence of an acid or alkali catalyst and water:

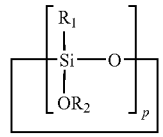 (1)

wherein,
R1 is a hydrogen atom, a $C_{1-3}$ alkyl group or a $C_{6-15}$ aryl group;
R2 is $SiX_1X_2X_3$ (wherein, each of $X_1$, $X_2$ and $X_3$ is, independently, a hydrogen atom, a $C_{1-10}$ alkyl group, a $C_{1-10}$ alkoxy group or a halogen atom, provided that at least one of them is hydrolysable); and
p is an integer from 3 to 8,

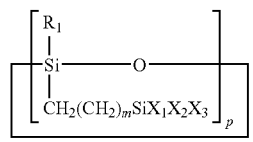 (2)

wherein,
$R_1$ is a hydrogen atom, a $C_{1-3}$ alkyl group or a $C_{6-15}$ aryl group;
each of $X_1$, $X_2$ and $X_3$ is, independently, a hydrogen atom, a $C_{1-3}$ alkyl group, a $C_{1-10}$ alkoxy group or a halogen atom, provided that at least one of them is hydrolysable;
m is an integer from 0 to 10; and
p is an integer from 3 to 8, $X_3X_2X_1Si\text{-}M\text{-}SiX_1X_2X_3$ (3)

wherein,
each of $X_1$, $X_2$ and $X_3$ is, independently, a hydrogen atom, a $C_{1-3}$ alkyl group, a $C_{1-10}$ alkoxy group or a halogen atom, provided that at least one of them is hydrolysable; and
M is a single bond, a $C_{1-10}$ alkylene group, or a $C_{6-15}$ arylene group, $(R_1)_q Si(OR_2)_{4-q}$ (4)

wherein,
$R_1$ is a hydrogen atom, a $C_{1-3}$ alkyl group, a $C_{6-15}$ aryl group or a halogen atom,
R2 is a hydrogen atom, a $C_{1-3}$ alkyl group or a $C_{6-15}$ aryl group, provided that at least one of them is hydrolysable; and
q is an integer from 0 to 3, and

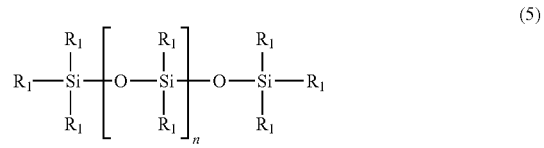 (5)

wherein,
each of $R_1$ is a hydrogen atom, a $C_{1-3}$ alkyl group, a $C_{1-10}$ alkoxy group, a hydroxy group or a halogen atom, provided that at least one of them is hydrolysable; and
n is an integer from 0 to 30.

3. The process according to claim 2, wherein the pore-generating material is selected from the group consisting of cyclodextrin, polycaprolactone, Brij-based surfactant, polyethyleneglycol-polypropylene-glycol-polyethyleneglycol triblock copolymer surfactant, and derivatives and mixtures thereof.

4. The process according to claim 2, wherein the liquid coating composition comprises 0-70 wt % of the pore-generating material based on total weight of the solid matter (inclusive of the siloxane-base polymer and the pore-generating material).

5. The process according to claim 2, wherein the organic solvent is an aliphatic hydrocarbon solvent such as hexane or heptane; an aromatic hydrocarbon solvent such as anisol, mesitylene or xylene; a ketone-based solvent such as methyl isobutyl ketone, 1-methyl-2-pyrrolidinone, cyclohexanone or acetone; an ether-based solvent such as tetrahydrofuran or isopropyl ether; an acetate-based solvents such as ethyl acetate, butyl acetate or propylene glycol methyl ether acetate; an alcohol-based solvent such as isopropyl alcohol or butyl alcohol; an amide-based solvent such as dimethylacetamide or dimethylformamide; a silicon-based solvent; or a mixture thereof.

6. The process according to claim 2, wherein the liquid coating composition comprises 5-70 wt % of the solid matter (inclusive of the sioxane-base polymer and the pore-generating material) based on total weight of the composition.

7. The process according to claim 2, wherein the heat-curing is performed at 150-600° C. for 1-180 minutes.

8. A dielectric film produced by the process according to claim 2.

* * * * *